United States Patent
Matsumoto et al.

(10) Patent No.: US 7,926,947 B2
(45) Date of Patent: Apr. 19, 2011

(54) OPHTHALMIC EXAMINATION SYSTEM

(75) Inventors: Chota Matsumoto, Tondabayashi (JP); Hiroshi Yuuki, Kobe (JP)

(73) Assignees: Chota Matsumoto, Osaka (JP); Shinko Seiki Company, Limited, Kobe-Shi, Hyogo (JP)

( * ) Notice: Subject to any disclaimer, the term of this patent is extended or adjusted under 35 U.S.C. 154(b) by 0 days.

(21) Appl. No.: 12/665,002

(22) PCT Filed: Jun. 28, 2007

(86) PCT No.: PCT/JP2007/062991
§ 371 (c)(1),
(2), (4) Date: Dec. 16, 2009

(87) PCT Pub. No.: WO2009/001458
PCT Pub. Date: Dec. 31, 2008

(65) Prior Publication Data
US 2010/0182570 A1 Jul. 22, 2010

(51) Int. Cl.
*A61B 3/02* (2006.01)
(52) U.S. Cl. .................... 351/237; 351/224; 351/239
(58) Field of Classification Search .............. 351/222, 351/223, 224, 237, 238, 239, 242, 243
See application file for complete search history.

(56) References Cited

U.S. PATENT DOCUMENTS
7,441,900 B2   10/2008   Mihashi et al.
2004/0095556 A1 *  5/2004   Mihashi et al. .............. 351/238

FOREIGN PATENT DOCUMENTS
JP  02-004308 A   1/1990
JP  2002-233502 A   8/2002
JP  2005-102946 A   4/2005
JP  2006-340755 A   12/2006

* cited by examiner

*Primary Examiner* — Huy K Mai
(74) *Attorney, Agent, or Firm* — Duane Morris LLP

(57) ABSTRACT

An unpolarized light beam emitted from a target presenting light source (12) is collimated by a collimator lens (20), and is made to be incident on a target presenting liquid crystal shutter (22), while an unpolarized light beams emitted from a background presenting light source (14) is collimated by a collimator lens (30), and is made to be incident on a background presenting liquid crystal shutter (32). The liquid crystal shutters (22, 32) have shutter patterns which are reverses to each other. The target and background light beams emerging from said liquid crystal shutters (22, 32) are combined with each other, together with their polarization states, by a half prism (24) acting as combining means. The resultant unpolarized light beam resulting from the combining is projected through a magnifying optical system (26) onto an eye to be examined. Since an unpolarized light beam is projected onto the eye, reliable examination, unaffected by polarization, can be realized.

4 Claims, 4 Drawing Sheets (a) Image with Target with Maximum Brightness (b) Image with Target with Minimum Brightness (c) Image with Target with Intermediate Brightness

OPHTHALMIC EXAMINATION SYSTEM

TECHNICAL FIELD

This invention relates to an ophthalmic examination system and, more particularly, to an ophthalmic examination system in which a visual target for use in examination is presented to an eye to be examined in order to examine the eye based on how the eye visually recognizes the target.

BACKGROUND ART

An example of such ophthalmic examination systems is disclosed in Patent Literature 1. The arrangement disclosed in this Patent Literature 1, the one according to the third embodiment shown in its FIG. 9, in particular, is very simple and includes a light source for presenting the visual target and a light source for presenting the background to the target. The target light source is arranged to blink, and the light beam from this light source is collimated by a collimator lens. After that, only an S (Senkrecht) polarization component is extracted from the collimated light beam by a polarizing plate, before it impinges on the incident surface of a liquid crystal shutter. The liquid crystal shutter includes shutter pattern including a transmissive region, e.g. a circular region, having an area sufficiently smaller than the effective area of the incident surface, and a remaining, blocking region. Only the light (S-polarized light) beam incident on the transmissive region of the incident surface provided with the shutter pattern passes through the liquid crystal shutter and emerges out from the emerging surface. The emerging light beam is arranged to be incident on a polarizing prism acting as combining means.

The background presenting light source has an arrangement similar to that of the target presenting light source and emits a light beam of a constant intensity same as the target presenting light source when it is on. The light beam emitted from this background presenting light source is collimated by another collimator lens. After that, only an S (Senkrecht) polarization component is extracted by another polarizing plate, before it impinges on the incident surface of another liquid crystal shutter. The liquid crystal shutter has a shutter pattern reverse to the one described above. Only the light beam (P-polarized light beam) incident on the transmissive region, corresponding to the above-described blocking region, of the incident surface provided with the shutter pattern, passes through the liquid crystal shutter and emerges out from the emerging surface. The emerging light beam, too, is incident on the above-described polarizing prism.

The polarizing prism has the boundary surface receiving the light beam emerging from each of the liquid crystal shutters, and emerging light beams are incident onto the boundary surface at angles, which are conjugate relative to each other. One of the incident light beams, i.e. the S-polarized light, is reflected at the boundary surface, whereas the P-polarized light beam for the background passes through the boundary surface. Thus, the S-polarized light beam reflected by the boundary surface and the P-polarized light beam passing through the boundary surface are combined. The resultant light beam is projected through a magnifying optical system onto the eye to be examined.

As a result, the blinking visual target and the background having the same brightness as the target when it is on are presented to the eye to be examined. In other words, the target is presented with brightness equal to or less than that of the background. Accordingly, when the target starts to blink, the amount of light incident on the eye to be examined does not increase, and, accordingly, a suppressed stimulus is given to the eye under examination. In this manner, erroneous recognition by the person receiving the examination caused by stimulus to the eye is reduced. (In other words, possibility of erroneously recognizing the target as if it were blinking at the instant the target just starts blinking.) Thus, the reliability of examination increases.

This feature is significantly advantageous in subjective examination, e.g. a visual field examination, for example. In subjective examinations including a visual field examination, a person receiving the examination operates a response button, for example, to notify an examiner that he or she has recognized the blinking of the target. Like this, the subjective examination in which the examination is based on such subjective indication by the person receiving the examination, and, therefore, the described prior technique in which the possibility of erroneous recognition can be reduced, is significantly effective for increasing the reliability (or precision) of the examination.

Patent Literature 1: JP 2006-340755A (Page 10, and FIG. 9)

DISCLOSURE OF THE INVENTION

Problem to be Solved by the Invention

However, according to the above-described prior technique, the visual target and the background presented to the eye to be examined are formed by linearly polarized light beams, namely S-polarized and P-polarized light beams, having different directions of polarization, and, therefore, depending on the incident angles of these S-polarized and P-polarized light beams onto the eye to be examined, the target and background are seen differently, which could adversely affect the reliability of the examination. Furthermore, in order to produce the S-polarized and P-polarized beams, two polarizing plates such as the ones described above must be used, which makes complicated the structure of the system as a whole.

Therefore, an object of this invention is to provide an ophthalmic examination system which makes it possible to carry out examination with higher reliability than prior systems. Other object of the invention is to make the structure of the system simpler than the prior systems.

Means to Solve the Problem

In order to achieve the objects, the present invention provides an ophthalmic examination system, in which a visual target for use in examination is presented to an eye to be examined and which makes the examination based on how the eye recognizes the target. The ophthalmic examination system according to the present invention is provided with visual target light generating means for generating a light beam forming the target, background light generating means for generating a background light beam forming a background to the target, and combining means for combining the target light beam generated by the target light generating means and the background light beam generated by the background light generated means and projecting the resultant light beam to an eye to be examined. The target light beam and the background light beam are unpolarized light beams like the natural light. The combining means is featured by combining the target and background light beams, keeping them unpolarized.

More specifically, according to the present invention, the unpolarized target light beam generated by the visual target light generating means and the unpolarized background light beam generated by the background light generating means are combined, while being kept unpolarized, and projected to an eye to be examined. Thus, the unpolarized, resultant light beam resulting from combining the unpolarized target and background light beams is projected to an eye to be examined. Thus, unlike the above-described prior technique affected by polarization, the system is not affected by the polarization. Also, the system according to the present invention does not need polarizing plates as required in the prior technique.

The combining means used in the present invention may have a boundary surface which receives incidence of the target and background light beams and which divides the respective light beams equally into transmitted light beams and reflected light beams, keeping their polarization states. In this case, the target and background light beams impinge on the boundary surface at angles conjugate relative to each other. One of first and second resultant light beams is projected onto the eye to be examined. The first resultant light beam results from combining the target light beam transmitted through the boundary surface with the background light beam reflected from the boundary surface, and the second resultant light beam results from combining the target light beam reflected by the boundary surface with the background light beam transmitted through the boundary surface.

When one of the first and second resultant light beams is projected onto the eye to be examined, monitoring means may be provided for monitoring the other of the first and second resultant light beams. With this arrangement, the target and background same as the ones presented to the eye to be examined are simultaneously monitored. Then, an operator operating the ophthalmic examination system of the present invention can know, from the data obtained by the monitoring, how the target and background are presented to the eye to be examined. The results of the monitoring with the monitoring means are very useful in, for example, adjusting the positions of the target light generating means, the background light generating means and the combining means.

The combining means used in the present invention may be an unpolarizing beam splitter, e.g. a half prism and a half mirror.

The present invention can be suitably embodied in a perimeter for measuring a filed of view of the eye to be examined.

BEST MODE FOR CARRYING OUT INVENTION

An embodiment of the present invention is described with reference to a static perimeter by way of example.

Figure 1:
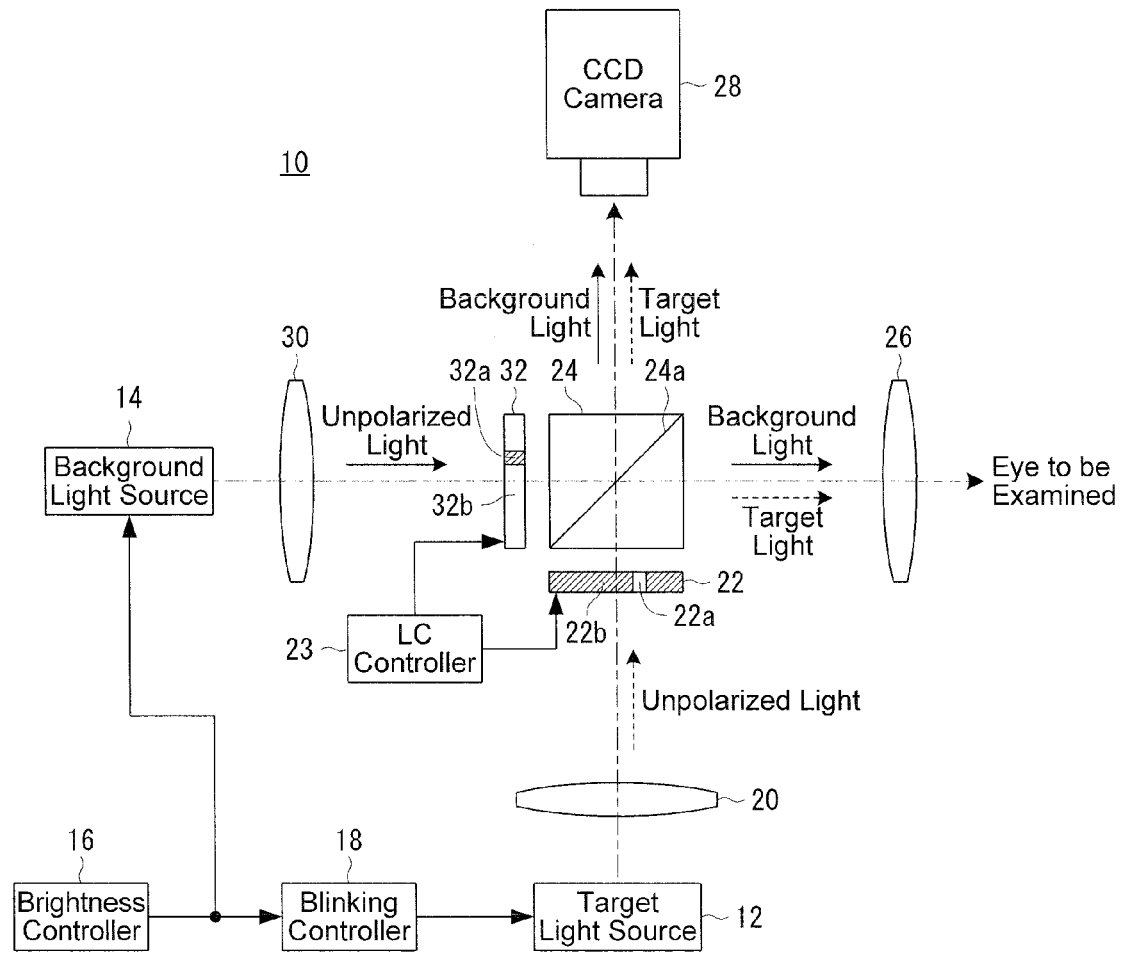
FIG. 1 illustrates a schematic arrangement of a perimeter according to an embodiment of the present invention.

As shown in FIG. 1, a perimeter 10 according to an embodiment of the present invention includes two light sources 12 and 14. The light sources 12 and 14 are of the same specifications and, specifically, they are what is called RGB-LED light sources, including a two-dimensional array of a number of red-emitting diodes, a number of green-emitting diodes, and a number of blue-emitting diodes. The brightness of each of the light sources 12 and 14 can be controlled through a common light-source controller 16. The colors of light emitted by the light sources 12 and 14, too, can be controlled through the light-source controller 16. Usually, they have white color similar to the natural light.

A blinking controller 18 is connected between one of the light sources, namely, the light source 12, and the light-source controller 16, for making the light source 12 blink. More specifically, the blinking controller 18 controls the light source 12 in such a manner that it sinusoidally changes between a first state in which it emits light with the same brightness as the light source 14, and a second state in which the light source 12 does not emit light. In this manner, the light source 12 gradually blinks sinusoidally. The cycle of blinking of the light source 12 provided by the blinking controller 18 is controllable to be a desired cycle in a range of, for example, 1 Hz and 120 Hz in terms of frequency.

Figure 2:
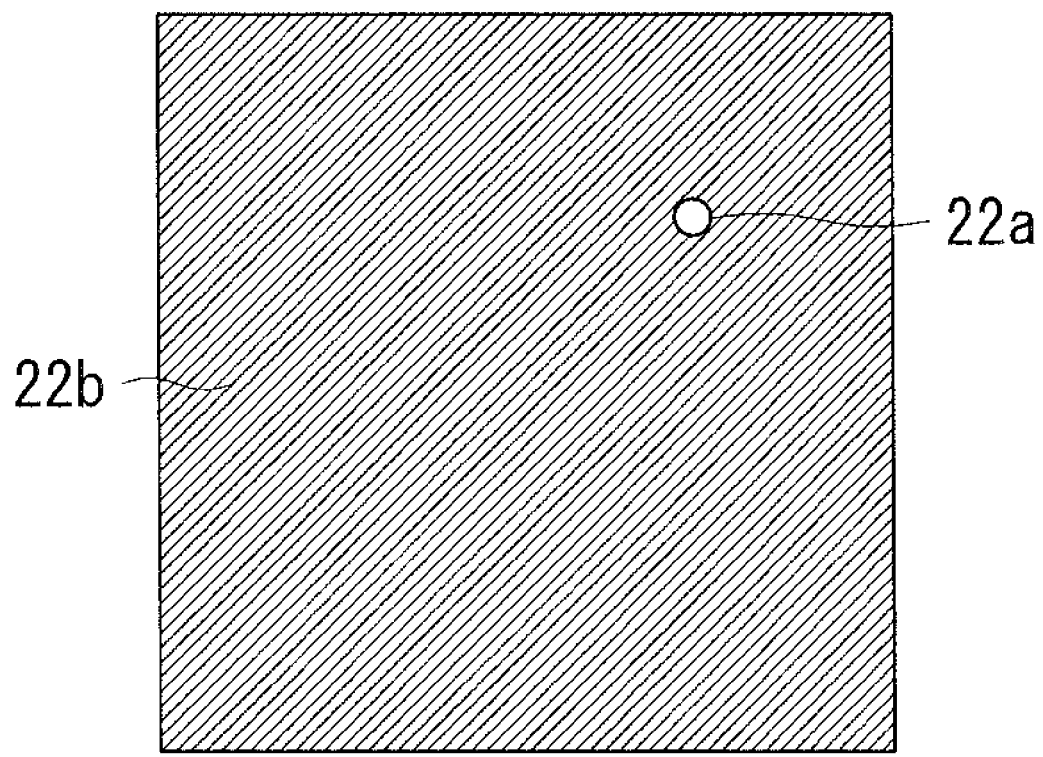
FIG. 2 is an illustration of an example of a shutter pattern provided by a visual target presenting liquid crystal shutter according to the embodiment.

The light source 12 blinking in the described manner is for presenting a visual target 100 (see FIG. 4) described later, and an unpolarized light beam emitted from the target presenting light source 12 is collimated by a collimator lens 20 and impinges on an incident surface (the downward surface in FIG. 1) of a target presenting liquid crystal (LC) shutter 22. The liquid crystal shutter 22 forms a shutter pattern as, for example, the one shown in FIG. 2, on its incident surface in accordance with a target presenting shutter control signal provided by a liquid crystal controller 23. Specifically, only a circular region 22a sufficiently small in area relative to the effective area of a rectangular incident surface, is made transmissive, with the remaining region 22b being light-blocking. Thus, only the light incident on the transmissive region 22a in the incident surface with such shutter pattern formed thereon passes the liquid crystal shutter 22 and goes out from the emerging surface (the upward surface in FIG. 1), whereas the light impinging on the blocking region 22b is blocked and, therefore, does not emerge from the shutter 22. The position of the transmissive region 22a can be changed as desired.

The light beam passing through the liquid crystal shutter 22 (i.e. the light beam going out of the outgoing surface of the liquid crystal shutter 22), or what we may call a target light beam, is made to impinge on a cubic half prism 24 acting as combining means. Specifically, the half prism 24 has the boundary surface 24a, and the target light beam impinges on the boundary surface 24a at an angle of incidence of 45 degrees. The target light beam incident on the boundary surface 24a is equally divided into transmitted and reflected light beams together with its polarization. The reflected light beam advances in the direction perpendicular to the direction of incidence of the target light beam onto the boundary surface 24a, and passes through a magnifying optical system 26 before impinging onto an eye to be examined (not shown). Although not shown in detail in the drawings, the magnifying optical system 26 includes a focus adjusting lens, which is movable along its optical axis for focus adjustment to make the eye to be examined (i.e. the retina) and the outgoing surface of the liquid crystal shutter 22 conjugate with each other, or, in other words, to make the focus of the eye to be examined coincide with the outgoing surface of the liquid crystal shutter 22.

The transmitted light beam advances in the same direction as the target light beam incident on the boundary surface 24a and enters into a CCD (Charge Coupled Device) camera 28 acting as monitoring means. The CCD camera also includes a focus adjusting lens, of which focus point is adjusted to be on the outgoing surface of the liquid crystal shutter 22.

Figure 3:
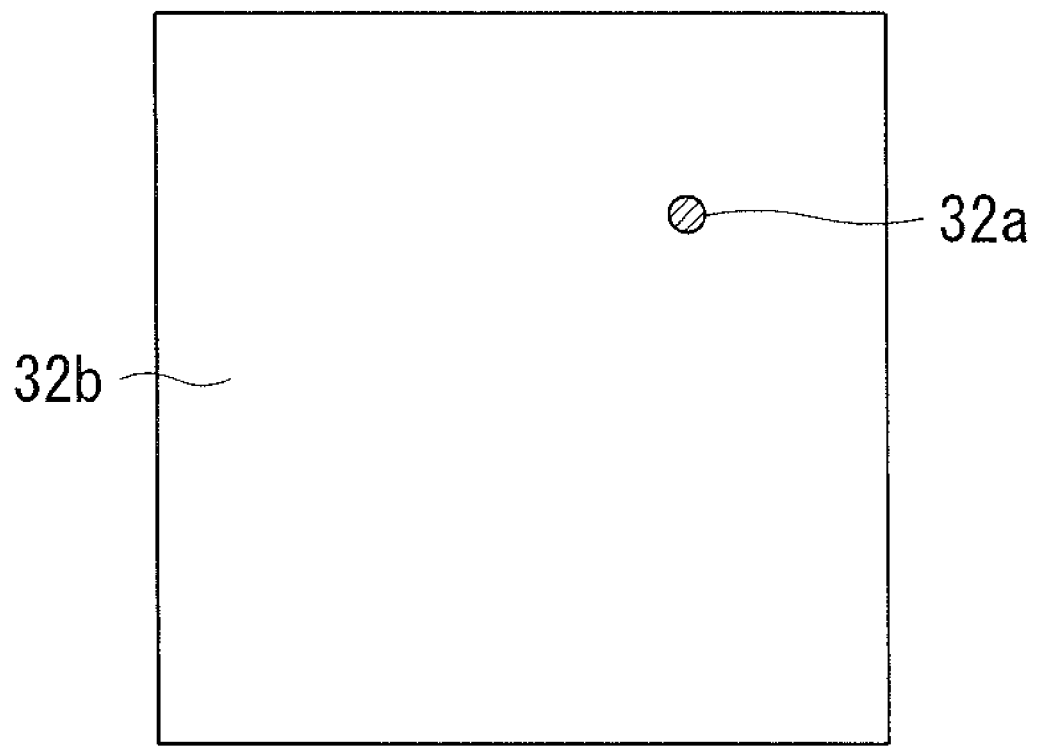
FIG. 3 is an illustration of an example of a shutter pattern provided by a background presenting liquid crystal shutter according to the embodiment.

The other light source 14 is for presenting the background 102 FIG. 4) described later. An unpolarized light beam emitted from the background presenting light source 14 is collimated by another collimator lens 30 and impinges on an incident surface of a background presenting liquid crystal shutter 32 (i.e. the left side surface of the shutter 32 in FIG. 1). The liquid crystal shutter 32 is of the same specifications as the target presenting liquid crystal shutter 22, and forms a shutter pattern, which is reverse to the shutter pattern provided by the target presenting liquid crystal shutter 22, on its incident surface in accordance with a background presenting shutter control signal provided by the liquid crystal controller 23. Specifically, as shown in FIG. 3, the shutter pattern is composed of a blocking region 32a, which is a portion of an effective area of the rectangular incident surface and corresponds to the transmissive region 22a of the target presenting liquid crystal shutter 22, and a transmissive region 32b, which is the remaining portion of the effective area. Only a portion incident on the transmissive region 32b, out of the light beam incident on the incident surface with such shutter pattern formed thereon, passes through the liquid crystal shutter 32 and emerges from the emerging surface (on the right side surface in FIG. 1). The portion of the light beam incident on the blocking region 32a does not emerge. It should be noted that the position of the blocking region 32a can be changed in operative association with the transmissive region 22a of the target presenting liquid crystal shutter 22.

The light beam passing through the background presenting liquid crystal shutter 32 (i.e. the light beam emerging from the emerging surface of the liquid crystal shutter 32), or the background light beam, is also led to the half prism 24. More specifically, the background light beam is caused to impinge onto the boundary surface 24a of the half prism 24 from the side opposite to that onto which the target light beam impinges, at an angle orthogonal to the direction of incidence of the target light beam, or, in other words, at an angle conjugate with the angle of incidence of the target light beam. The background light together with its polarization state is equally divided into transmitted and reflected light beams, too. The transmitted light advances in the direction same as the direction of incidence of the background light beam onto the boundary surface 24a, and is combined with the target light beam reflected by the boundary surface 24a. The resultant light beam passes through the magnifying optical system 26 and, then, impinges onto the eye to be examined. The distance from the eye to be examined to the light emerging surface of the background presenting liquid crystal shutter 32 is equal to the distance from the eye to the light emerging surface of the target presenting liquid crystal shutter 22. Accordingly, when the focus adjusting lens of the magnifying optical system 26 is used to focus the eye on the light emerging surface of the target presenting liquid crystal shutter 22, the eye is focused on the light emerging surface of the background presenting liquid crystal shutter 32, too, as a matter of course.

The background light reflected from the boundary surface 24a advances in the direction orthogonal to the direction of incidence of the background light beam onto the boundary surface 24a, and is combined with the target light beam transmitted through the boundary surface 24a. The resultant light beam impinges on the CCD camera 28. It should be noted that, as described above, when the CCD camera 28 is focused on the emerging surface of the target presenting liquid crystal shutter 22, the focus of the CCD camera 28 is on the emerging surface of the background presenting liquid crystal shutter 32.

Figure 4:
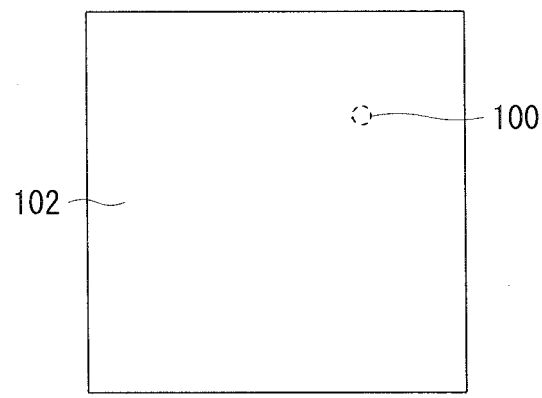
FIG. 4 illustrates examples of images presented to an eye to be examined.
Figure 4:
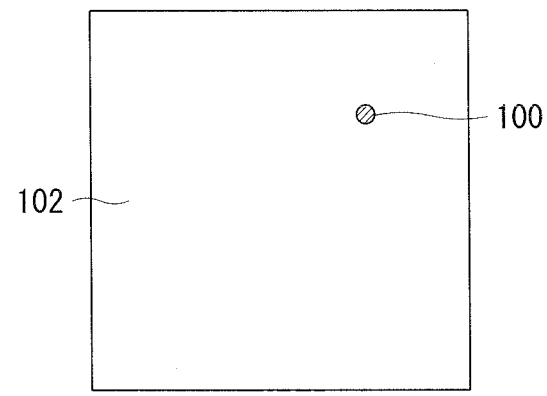
Figure 4:
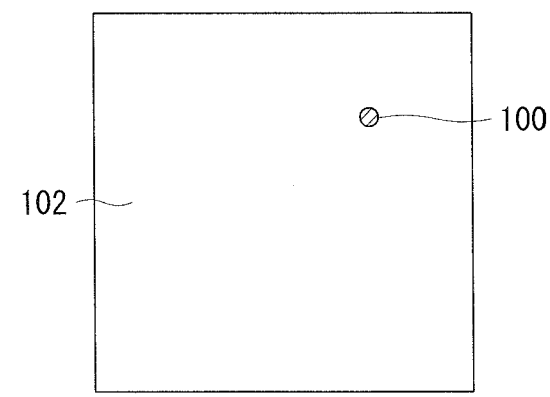

The projection, onto the eye to be examined, of the combination of the target light beam reflected from the boundary surface 24a of the half prism 24 and the background light beam transmitted through the boundary surface 24a, in the manner described above, causes an image like the ones shown in FIG. 4 to be presented to the eye. More specifically, when the target presenting light source 12 is emitting light of the same intensity as the background presenting light source 14 (i.e. the maximum brightness), an image of brightness uniform over the entire visual field of the eye as shown in FIG. 4(a) is presented to the eye. This image is formed by presenting a target 100, indicated by a broken line circle in FIG. 4(a), with the same brightness as the remaining region or background 102. The circular target 100 corresponds to the transmissive region 22a of the target presenting liquid crystal shutter 22 and the blocking region 32a of the background presenting liquid crystal shutter 32.

When the target presenting light source 12 is not emitting light, the target 100 appears darker than the background 102 (i.e. with the minimum brightness), as shown in FIG. 4(b). In other words, an image with a region corresponding to the target 100 missing is presented.

The images shown in FIG. 4(a) and FIG. 4(b) are alternately presented to the eye in accordance with the blinking cycle of the target presenting light source 12, resulting in blinking of the target 100. As described above, the target presenting light source 12 sinusoidally blinks slowly, and, accordingly, the target 100, too, sinusoidally blinks slowly. In other words, the target 100 changes its brightness slowly as shown in FIG. 4(c), when it changes from one of the states shown in FIGS. 4(a) and 4(b) to the other.

At the same time, the target light beam passing through the boundary surface 24a of the half prism 24 and the background light beam reflected from the boundary surface 24a are combined and enter into the CCD camera 28, so that the same images as shown in FIG. 4 are taken into the CCD camera 28. The image taken by the CCD camera 28 may be displayed on a monitor screen (not shown), for example.

The perimeter 10 with the above-described arrangement is used to examine a field of view in the following manner. The blinking of the target 100 is started with an eye of a person to be examined positioned in the beam exit side of the magnifying optical system 26. The person to be examined pushes a button (not shown), for example, when he or she sees the target 100 blink. An operator, who is an examiner, can know from the state of the button whether or not the person to be examined is recognizing the blinking of the target 100. This operation is repeated with the position of the target 100 changed appropriately, whereby the visual field of the examined person is measured.

The target 100 is presented to the eye with brightness at least same as or lower than that of the background 102. Accordingly, when the blinking of the target 100 is initiated, it never occurs that the amount of light entering into the eye to be examined increases, so that the stimulation to the eye can be reduced, whereby erroneous recognition by the person examined which could be caused by intense stimulation to the eye can be reduced, resulting in improvement of precision of examination. This is significantly advantageous in subjective examinations like visual field examinations.

In addition, the target 100 and background 102 presented to the eye to be examined are provided by a combination of unpolarized light beams, namely, an unpolarized target light beam and an unpolarized background light beam. Therefore, even when the angle of incidence of the resultant light beam combination onto the eye to be examined changes, the appearances to the eye of the target 100 and the background 102 do not change. In contrast, according to the aforementioned prior technique, the target and the background are provided by S- and P-polarization light beams, which are linearly polarized light beams having different directions of polarization, the target and background may be seen to the eye different, depending on the angles of incidence, onto the eye, of the S-polarization beam and the P-polarization beam. Thus, the perimeter 10 according to the present invention can provide visual field examination of high reliability than the prior technique.

The system of the described embodiment is free from influence of polarization because the half prism 24 is used as the combining means. In addition to this advantage, different from the polarizing prism used as the combining means in the prior technique, the half prism 24 does not have ripples, which is usually thought to be a disadvantageous property, and, therefore, the system is free of influence of ripples.

Also, since the same image as presented to the eye being examined is displayed on the above-mentioned monitor screen, the operator of the system can know the image simultaneously presented to the eye being examined currently, by watching the monitor screen. This function, which may be called a real-time monitoring function, is advantageously used when, for example, adjusting the positions of the components of the perimeter 10 of the present embodiment, such as the liquid crystal shutters 22 and 32, in particular. It can be readily understood that this real-time monitoring function is realized by the use of the half prism 24 as the combining means.

As described above, the system according to the described embodiment is not affected by the polarization of light impinging on the eye to be examined, different from the prior technique, it enables visual field examination with higher reliability than the described prior technique. Furthermore, the system has improved workability because of the above-described real-time monitoring function. Also, different from the described prior technique, the overall structure of the perimeter 10 can be simplified because it does not require polarizing plates as used to derive the S- and P-polarization components in the prior technique.

It should be noted that during visual field examination, by appropriately changing the blinking cycle of the target 100, or appropriately changing the brightness of the target 100 and the light source 12 (or, in other words, the relative difference between the brightness of the target 100 and the brightness of the background 102 when the target presenting light source 12 is not emitting light), or their color, more precise examination can be realized. It should be also noted that, although not shown, a view fixing target (gazing point) for use in fixing the gazing point of an eye to be examined, is presented in addition to the target 100 during the visual field examination.

The angle of view of an image presented to an eye to be examined in the described embodiment is sufficiently wider than the field of view of the eye to be examined, and it is, for the horizontal direction, about 60 degrees in each of the left and right directions (the sum being 120 degrees) for example, and is, for the vertical direction, also about 60 degrees in the upward and downward directions (the sum being 120 degrees), for example. Needless to say, the angles are not limited to these values.

Although the half prism 24 is used as the combining means in the described embodiment, a planar half mirror may be used instead. When a half mirror is used, the optical axis changes due to refraction of light depending on the thickness of the half mirror. In view of such disadvantage, the half prism 24 is more suitable.

Although the target 100 is caused to blink sinusoidally in the described embodiment, it may be arranged to blink along other waveforms, such as a sawtooth waveform, or a pulse waveform. Further, according to the described embodiment, the light source 12 to present the target is blinked to blink the target 100, but other means may be employed instead. For example, blocking means, e.g. a chopper, which operates to intermittently interrupt the target light may be disposed between the target presenting light source 12 and the collimator lens 20, or between the collimator lens 20 and the target presenting liquid crystal shutter 22, or between the liquid crystal shutter 22 and the half prism 24. In an alternative arrangement, the transmissive region 22a of the target presenting liquid crystal shutter 22 may be intermittently made to be a blocking region to thereby make the target 100 blink.

When the blocking means, e.g. a chopper, is used, or the transmissive region 22a of the target presenting liquid crystal shutter 22 is intermittently made to be a blocking region, as described above, one of the target presenting light source 12 and the background presenting light source 14 may be used also for the other. In other words, only one light source is used, with a light beam from this single light source divided into two by means of dividing means, such as a half prism, and one of the resultant two light beams is used for presenting the target, and the other for presenting the background.

Although RGB-LED light sources are used as the light sources 12 and 14 in the described embodiment, other light sources, such as white LEDs, incandescent lamps, and halogen lamps, may be used instead. When such what-is-called one-color light sources are used, optical color filters may be used to change the colors of the target 100 and the background 102. Furthermore, instead of using such optical color filters, color type liquid crystal shutters may be used as the liquid crystal shutters 22 and 32 so that the colors of the target 100 and the background 102 can be changed.

Furthermore, instead of using the liquid crystal shutters 22 and 32, means performing equivalent functions or pattern-forming means may be used. For example, a micromirror device including a number of two-dimensionally arranged minute mirrors having individually controllable angles, may be used as the pattern-forming means.

The shape of the target 100 (i.e. the shape of the transmissive region 22a of the target presenting liquid crystal shutter 22 and of the blocking region 32a of the background presenting liquid crystal shutter 32) is circular in the described embodiment, but it is not limited to circle. It may be of other shape, e.g. elliptic, rectangular, triangular, starlike, or linear. Further, a plurality of targets 100 may be simultaneously presented. The number and size of the target 100 may be settable as desired.

The invention is not limited to the use of the CCD camera 28 as the monitoring means, but, in place of the CCD camera 28, a system similar to the magnifying optical system 26 may be used, through which an image same as the one projected onto the eye to be examined may be monitored directly. In an alternative arrangement, means onto which an image is projected, e.g. a screen, may be used so that the image can be directly displayed on such means.

The brightness controller 16, the blinking controller 18 and the liquid crystal controller 23 may be discretely arranged, or they may be provided by, for example, a personal computer.

What is claimed is:

1. An ophthalmic examination system for examining an eye to be examined, in which an image containing an examination target is presented to said eye to be examined and the eye is examined based on how the eye sees the target;
said ophthalmic examination system comprising:
target light generating means generating an unpolarized target light beam for forming said target in said image;

background light generating means generating an unpolarized background light beam for forming a background which is the region of said image excluding said target; and combining means for combining said target and background light beams and projecting the resultant light beam to said eye to be examined;

wherein:

said combining means has a boundary surface which receives incidence of said target and background light beams and divides each of said incident target and background light beams equally into transmitted and reflected light beams without changing the polarization state thereof; said target and background light beams are incident on said boundary surface at angles which are conjugate with each other; and either one of first and second resultant light beams is projected onto said eye to be examined, said first resultant light beam resulting from combining said target light beam as transmitted through said boundary surface and said background light beam as reflected from said boundary surface, said second resultant light beam resulting from combining said target light beam as reflected from said boundary surface and said background light beam as transmitted through said boundary surface.

2. The ophthalmic examination system according to claim 1, further comprising monitoring means for monitoring the other of said first and second resultant light beams.

3. The ophthalmic examination system according to claim 1, wherein said combining means is a half prism.

4. The ophthalmic examination system according to claim 1, wherein said ophthalmic examination system is a perimeter for measuring the field of view of said eye to be examined.

* * * * *